United States Patent [19]

Gassen et al.

[11] Patent Number: 5,171,901
[45] Date of Patent: Dec. 15, 1992

[54] PROCESS FOR THE PREPARATION OF 1,1,1,3,3,3-HEXAFLUOROPROPANE AND 2-CHLORO-1,1,1,3,3,3-HEXAFLUOROPROPANE

[75] Inventors: Karl-Rudolf Gassen, Odenthal; Dietmar Bielefeldt, Ratingen; Albrecht Marhold, Leverkusen; Hans-Helmut Schwarz, Krefeld, all of Fed. Rep. of Germany

[73] Assignee: Bayer Aktiengesellschaft, Leverkusen, Fed. Rep. of Germany

[21] Appl. No.: 804,471

[22] Filed: Dec. 5, 1991

Related U.S. Application Data

[63] Continuation of Ser. No. 651,665, Feb. 6, 1991, abandoned.

[30] Foreign Application Priority Data

Feb. 14, 1990 [DE] Fed. Rep. of Germany ....... 4004495

[51] Int. Cl.$^5$ ............................................. C07C 17/08
[52] U.S. Cl. ................................... 570/168; 570/169; 570/165
[58] Field of Search ................ 570/168, 167, 169, 165

[56] References Cited

U.S. PATENT DOCUMENTS 2,942,036 6/1960 Smith .................................. 570/176
4,766,260 8/1988 Manzer et al. ...................... 570/168

FOREIGN PATENT DOCUMENTS 0347830 12/1989 European Pat. Off. ............ 570/176
4872105 12/1971 Japan .................................... 570/168
623227 5/1949 United Kingdom ................ 570/167

Primary Examiner—Alan Siegel
Attorney, Agent, or Firm—Sprung Horn Kramer & Woods

[57] ABSTRACT

Hexafluoropropanes of the formula $CF_3\text{-}CHX\text{-}CF_3$ where X is hydrogen or chlorine are prepared by reacting hexachloropropene with hydrogen fluoride in the gas phase in the presence of a catalyst.

6 Claims, No Drawings

PROCESS FOR THE PREPARATION OF 1,1,1,3,3,3-HEXAFLUOROPROPANE AND 2-CHLORO-1,1,1,3,3,3-HEXAFLUOROPROPANE

This application is a continuation of application Ser. No. 651,665, filed Feb. 6, 1991 now abandoned.

The hexafluoropropanes mentioned in the title have previously only been obtainable by expensive processes, using starting materials which are difficult to obtain and/or in poor yields. Thus, J. Org. Chem. 28, 112 (1963) describes that 1,1,1,3,3,3-hexafluoropropane can be obtained only in about 20% yield from hexachloropropane and pentachloropropene by reaction with potassium fluoride in the presence of a polar solvent.

J. Org. Chem. 54, 1432 (1989) describes the preparation of 2-chloro-1,1,1,3,3,3-hexafluoropropane from 1,1,1,3,3,3-hexafluoro-2-propanol, which is first converted to the corresponding nonaflate compound (i.e. a nonafluorobutanesulphonate) into which a chlorine atom is then introduced in the 2-position using lithium chloride in the presence of a crown ether.

1,1,1,3,3,3-Hexafluoropropane and 2-chloro-1,1,1,3,3,3-hexafluoropropane increasingly are gaining interest in industry—the former compound as a propellant which does not endanger the ozone layer of the atmosphere (see Bild der Wissenschaften 2, 49 (1988)) and the latter compound as a heat exchanger liquid (see EP-A 72,308). There is therefore a need for a technically advantageous preparation process for these substances.

A process has now been found for the preparation of hexafluoropropanes of the formula (I)

$$CF_3-CHX-CF_3 \quad (I)$$

in which

X represents hydrogen or chlorine, which process is characterised in that hexachloropropene is reacted with hydrogen fluoride in the gas phase in the presence of a catalyst.

The starting material hexachloropropene is available at low cost, since it is obtainable from simple base chemicals (for example from chloroform and tetrachloroethane).

A suitable form of hydrogen fluoride is commercially available hydrogen fluoride. It can be used as such but also in dilute form, for example mixed with nitrogen.

According to the invention, both reactants are reacted in the gas phase. Suitable reaction temperatures are, for example, those in the range from 250° to 600° C. Preferably, the reaction is carried out in the range from 300° to 550° C., in particular in the range from 350° to 500° C.

The process according to the invention can be carried out at any desired pressures in the reaction zone, as long as the reactants remain in the gas phase at the pressure chosen in each case. Preferably, the pressure used is 1 to 3 bar, in particular atmospheric pressure or superatmospheric pressure corresponding to the flow resistance of the apparatus used.

The relative amounts of hexachloropropene and hydrogen fluoride used can be varied within wide limits. It is advantageous to use the hydrogen fluoride in excess, for example 5 to 100 mol of hydrogen fluoride per 1 mol of hexachloropropene. It is particularly preferred to use 10 to 50 mol of hydrogen fluoride per 1 mol of hexachloropropene.

Examples of suitable catalysts for the process according to the invention are halides and oxides of metals and transition metals. In particular, chlorides, fluorides and/or oxides of copper, chromium, iron, bismuth, zinc, lanthanum, cerium, zirconium, vanadium, molybdenum, tungsten and/or platinum which may have been mixed are suitable. Preference is given to chromium(III) salts alone or in a mixture with the metal chlorides, fluorides and/or oxides mentioned. The catalysts can be used as such, for example in pallet form, but can also be deposited on a support, for example on alumina, magnesium oxide, magnesium fluoride, calcium fluoride, zinc chloride and/or activated carbon.

Particular preference is given to chromium(III) salts, in particular chromium(III) fluorides, chromium(III) chlorides and chromium(III) oxides on one of the support materials mentioned.

The flow rate of the reaction mixture and the catalyst amount can be chosen such, for example, that catalyst charges of 50 to 1000 g/1×h, preferably 150 to 500 g/1×h, are obtained.

Suitable materials for the reaction and secondary apparatuses are materials which are resistant to the attack of hydrogen fluoride and hydrogen chloride even at high temperatures, for example nickel, chromium and/or molybdenum steels, and pure nickel.

The reaction according to the invention can be carried out, for example, by heating the starting materials combined or separately to the reaction temperature, then passing them through a reaction zone (for example a heatable tube containing the catalyst), if desired washing the gas mixture leaving the reaction zone and cooling it, so that at least the organic components are condensed and, if desired, separating them further by distillation and purifying them.

After carrying out the process according to the invention, mixtures of fluorine- and/or chlorine-containing propanes and propenes are in general obtained. The propenes can be recycled into the reaction according to the invention.

The composition of the mixture leaving the reaction zone can be influenced by the reaction temperature. Particularly high proportions of 1,1,1,3,3,3-hexafluoropropane (formula (I), X=hydrogen) are obtained by carrying out the reaction at relatively high temperatures, for example at 435° to 525° C., in particular at 450° to 500° C.

Particularly high proportions of 2-chloro-1,1,1,3,3,3-hexafluoropropane are obtained by carrying out the reaction at relatively low temperatures, for example at 325° to 415° C., in particular at 350° to 400° C.

The process according to the invention enables the preparation of hexafluoropropanes of the formula (I) in a simple and low-cost manner. If the halogenated propenes present in the reaction mixture are recycled, hexafluoropropanes of the formula (I) can in general be obtained in yields of more than 80%, relative to the hexachloropropene used. If desired, $CF_3-CCl_2-CF_3$ and/or $CF_3-CHCl-CF_3$ can be separated off from the reaction mixture and hydrogenated catalytically either separately or in a mixture with 1,1,1,3,3,3-hexafluoropropane to give 1,1,1,3,3,3-hexafluoropropane.

This catalytic hydrogenation can be carried out in a manner known per se, for example by passing a mixture of hydrogen and $CF_3-CCl_2-CF_3$ and/or $CF_3-CHCl-CF_3$ over a fixed bed of hydrogenation catalyst. The molar ratio of hydrogenatable compounds to hydrogen can be, for example, 1:3 to 1:50. Preferably it is 1:4 to 1:20.

The hydrogenation can be carried out, for example, at atmospheric pressure or at superatmospheric pressures, for example in the range from atmospheric pressure to 20 bar. Preferably, it is carried out at atmospheric pressure.

Suitable hydrogenation catalysts are in particular those containing transition metals on support materials. Of the transition metals, palladium and platinum are preferred, in particular palladium. Examples of support materials are activated carbons, aluminas, silicas, barium sulphate, spinels, silicates and titanium dioxide. Activated carbons and lithium/aluminium spinels are preferred. The catalysts can contain, for example, 0.5 to 30 g of transition metal per litre of support material. Preferably, this content is in the range 2 to 20 g/l.

The flow rate of the hydrogenation mixture and the amount of catalyst can be chosen, for example, such that catalyst charges of 10 to 1000 g/l×h, preferably those of 50 to 500 g/l×h, are obtained. The reaction temperatures are in general above 20° C., preferably in the range 100° to 250° C.

The mixture formed in the hydrogenation can be worked up, for example, by washing it with water or dilute base to remove the hydrogen chloride formed and condensing the gaseous products, if desired after drying.

EXAMPLES

EXAMPLES 1 TO 4

40 g of hexachloropropene, 80 g of hydrogen fluoride and 1 l of nitrogen per hour were passed through a nickel tube containing 750 ml of a catalyst prepared according to Example 8 at the temperature given in each case. The gas mixture leaving the reaction zone was washed with water, dried, and the condensable portions were condensed at $-78°$ C.

The content of organic components in the condensate was determined by gas chromatography and by nuclear magnetic resonance spectroscopy. The following results were obtained:

| Composition of the isolated organic product (% by weight) | b.p. (°C.) | Example No. and reaction temperature | | | |
|---|---|---|---|---|---|
| | | 1 350° C. | 2 400° C. | 3 450° C. | 4 500° C. |
| $CF_3—CH_2—CF_3$ | −0.7 | — | 10 | 55 | 64 |
| $CF_3—CHCl—CF_3$ | 16 | 60 | 69 | 23 | 15 |
| $CF_3—CCl_2—CF_3$ | 33-34 | 1 | 3 | 6 | 7 |
| $CF_3—CCl=CF_2$ | 5 | 9 | 9 | 6 | 6 |
| $CF_3—CCl=CFCl$ | — | 15 | 5 | 6 | 4 |
| $CF_3—CCl=CCl_2$ | 89-91 | 15 | 4 | 4 | 4 |

If desired, the individual components can easily be separated by distillation

EXAMPLES 5 TO 7

An upright electrically heatable tubular quartz reactor (length 310 mm, diameter 36 mm) was charged with 200 ml of a supported catalyst containing 18 g of palladium per litre of a globular lithium/aluminium spinel (globule diameter 3 to 5 mm).

The catalyst was conditioned at 250° C. for 6 hours while passing 20 to 25 ml of hydrogen per hour through it. After that, the hydrogenations described below were carried out in each case. The gases leaving the quartz tube were condensed at $-78°$ C. and analysed by means of $^{19}$F-NMR spectroscopy.

EXAMPLE 5

Amounts used: 0.16 mol/h of $CF_3—CHCl—CF_3$ and 2.5 mol/h of hydrogen Reaction conditions: 200° C., atmospheric pressure Catalyst charge: 150 g/l×h $CF_3—CH_2—CF_3$ was obtained at a conversion of 95% and a selectivity of 94%.

EXAMPLE 6

Amounts used: 0.2 mol/h of $CF_3—CHCl—CF_3$ and 0.8 mol/h of hydrogen Reaction conditions: 200° C., atmospheric pressure Catalyst charge: 180 g/l×h $CF_3—CH_2—CF_3$ was obtained at a conversion of 92% and a selectivity of 85%.

EXAMPLE 7

Amounts used: 0.21 mol/h of $CF_3—CCl_2—CF_3$ and 1.1 mol/h of hydrogen
Reaction conditions: 200° C., atmospheric pressure
Catalyst charge: 200 g/l×h
$CF_3—CH_2—CF_3$ was obtained at a conversion of 89% and a selectivity of 87%.

EXAMPLE 8

300 g of $CrCl_3 \times 6\, H_2O$ and 30 g of $MgF_2$ were heated to 90° C. in 10 l of water. After 1 hour, 1300 g of an 11% strength aqueous ammonia solution were metered in. The mixture was then stirred for 1 hour, allowed to cool, and the precipitated solid was filtered off through a nutsche filter. The solid was washed twice with water, dried, powdered and mixed homogeneously with 2% by weight of graphite. This mixture was compacted to give tablets of 4 mm in size.

We claim:

1. A process for the preparation of hexafluoropropanes of the formula (I)

$$CF_3—CHX—CF_3 \quad (I)$$

in which
X represents hydrogen or chlorine, in which process hexachloropropene is reacted with hydrogen fluoride in the gas phase in the presence of a catalyst containing a chromium (III) salt, in which the reaction is carried out at from about 250° to 600° C.

2. The process of claim 1, in which 5 to 100 mol of hydrogen fluoride are used per 1 mol of hexachloropropene.

3. The process of claim 1, in which 1,1,1,3,3,3-hexafluoropropane is prepared by carrying out the reaction at 435° to 525° C.

4. The process of claim 1, in which 2-chloro-1,1,1,3,3,3-hexafluoropropane is prepared by carrying out the process at 325° to 415° C.

5. A process for the preparation of 1,1,1,3,3,3-hexafluoropropane, in which $CF_3—CCl_2—CF_3$ and/or $CF_3—CHCl—CF_3$ separated off from the reaction product mixture resulting from the process of claim 1 is hydrogenated catalytically.

6. The process of claim 5 in which transition metals or support materials are used as hydrogenation catalyst.

* * * * *